(12) United States Patent
Kikuchi

(10) Patent No.: US 7,225,810 B2
(45) Date of Patent: Jun. 5, 2007

(54) VALVE FOR USE IN HIGH PRESSURE GAS CONTAINERS

(75) Inventor: Toshiaki Kikuchi, Fuchu (JP)

(73) Assignee: Hamai Industries Limited, Tokyo (JP)

( * ) Notice: Subject to any disclaimer, the term of this patent is extended or adjusted under 35 U.S.C. 154(b) by 712 days.

(21) Appl. No.: 10/138,006

(22) Filed: May 2, 2002

(65) Prior Publication Data

US 2003/0131851 A1 Jul. 17, 2003

(30) Foreign Application Priority Data

Jan. 11, 2002 (JP) ............................. 2002-004947

(51) Int. Cl.
*A62B 9/02* (2006.01)
*A62B 9/00* (2006.01)

(52) U.S. Cl. .............................. 128/205.24; 128/205.22

(58) Field of Classification Search ........... 128/202.27, 128/201.28, 204.26, 205.18, 205.22, 205.24, 128/200.24, 204.18, 204.25, 207.12, 207.16, 128/203.25; 137/535, 536, 539, 540, 550, 137/614.02, 614.19, 630, 630.14, 630.15, 137/630.17, 630.18, 630.19, 636, 636.4, 137/538, 613
See application file for complete search history.

(56) References Cited

U.S. PATENT DOCUMENTS

| | | | | |
|---|---|---|---|---|
| 4,008,716 A | * | 2/1977 | Amlong | 128/205.24 |
| 4,061,160 A | * | 12/1977 | Kashmer et al. | 137/637.2 |
| 5,398,714 A | * | 3/1995 | Price | 137/102 |
| 5,662,100 A | * | 9/1997 | Fox et al. | 128/205.24 |
| 5,678,602 A | * | 10/1997 | Cannet et al. | 137/505.25 |
| 5,820,102 A | * | 10/1998 | Borland | 251/144 |
| 5,865,175 A | * | 2/1999 | Chu | 128/205.22 |
| 5,911,220 A | * | 6/1999 | Morgan et al. | 128/205.24 |
| 5,996,625 A | * | 12/1999 | Collado et al. | 137/614.19 |
| 6,230,737 B1 | * | 5/2001 | Notaro et al. | 137/329.4 |
| 6,240,951 B1 | * | 6/2001 | Yori | 137/224 |
| 6,364,161 B1 | * | 4/2002 | Pryor | 222/3 |
| 6,367,499 B1 | * | 4/2002 | Taku | 137/72 |
| 6,484,720 B1 | * | 11/2002 | Marquard et al. | 128/205.24 |
| 6,539,970 B1 | * | 4/2003 | Knowles et al. | 137/238 |
| 6,601,609 B2 | * | 8/2003 | Taylor | 137/614.2 |
| 6,752,152 B2 | * | 6/2004 | Gale et al. | 128/204.26 |
| 6,910,504 B2 | * | 6/2005 | Kroupa et al. | 137/636 |
| 6,986,350 B2 | * | 1/2006 | Zaiser et al. | 128/204.18 |
| 2003/0075179 A1 | * | 4/2003 | Gale et al. | 128/204.26 |
| 2005/0189022 A1 | * | 9/2005 | Kroupa et al. | 137/636 |
| 2005/0205140 A1 | * | 9/2005 | Hull et al. | 137/613 |

* cited by examiner

*Primary Examiner*—Teena K. Mitchell
(74) *Attorney, Agent, or Firm*—Norris, McLaughlin & Marcus PA

(57) ABSTRACT

An on-off valve mounted in a high pressurized gas container, which has a holding portion for holding a flow amount controlling member in a path formed in an upper stream side of the body of the valve, and in which a flow amount controlling member is movably held. In the flow amount controlling member, an orifice is formed. When the valve moves into an opening position, a high pressurized oxygen gas is flowed into a valve chamber by gas pressure, the flow amount controlling member moves and closes the path. At this time, the gas flow amount is restricted by the orifice, so that the pressurizing speed of the gas pressure at the down stream side of the orifice becomes slow and then heat generation due to the adiabatic compression is reduced.

7 Claims, 6 Drawing Sheets

VALVE FOR USE IN HIGH PRESSURE GAS CONTAINERS

BACKGROUND OF THE INVENTION

1) Field of the Invention

The present invention relates to an on-off valve for use in high pressure gas vessels, More particularly, This invention relates to an on-off valve where the flow amount of gas is restricted when the valve is made off.

2) Prior Art

Accidents due to ignition in high pressure vessels sometime occur when oxide gas is removed from the gas vessels. The following are considered causes of such accidents: (1) An Oxide per se is an essential for ignition; (2) when a highly pressures gas flows into an airtightened space of an apparatus, which is connected to the outlet side of the operation valve of a high pressure vessel heat is instantaneously generated due to adiabatic compression; and (3) the sealing member or lubricant of the valve, or dust in the valve acts as an ignition material.

In order to prevent such accidents, cautions are known such that when opening the valve of such a high pressure vessels the operating handle should be slowly moved into the opening direction in order to decrease the gas pressure gradually in the space at the downstream side of the valve.

However, when using oxygen bombs for medical use, for example, it is necessary to supply oxygen to patients in an emergency, so that the operator cannot pay attention to the caution that the operation valve should be opened slowly.

Further, such oxygen bombs for medical uses are mostly equipped in ambulance cars or carried together with patients who are being brought to a hospital, therefore these bombs are so designed as to be made compact, taking transportation convenience into consideration. In such compact oxygen bombs, the operating valves are also made compact and the operating handles to turn the valve on or off are also small, making it difficult to grasp. Therefore, it is particularly difficult to rotate the handle slowly in the opening direction and to conduct a delicate operation by hand.

SUMMARY OF THE INVENTION

The present invention has for its purpose to provide a high pressure gas vessel, where the generation of an adiabatic compression heat of high pressurized oxygen gas is reduced even when the valve is opened rapidly.

This purpose is carried out by the present invention mentioned below.

(1) A valve for use in high pressure gas containers comprises:
  - an inlet being connected to an inside of a high pressure gas container;
  - an outlet being connected to an airtightened space;
  - an operation mechanism for controlling an air fluency between said inlet and said outlet in a closing condition or in an opening condition being provided between said inlet and said outlet;
  - a gas introducing path for connecting said operation mechanism and said inlet;
  - a gas exiting path for connecting to said operation mechanism and said outlet;
  - a container portion being provided in said gas introducing path;
  - a gas flow amount control member for reducing an upper limit amount of gas which is flowing through said gas introducing path being movably contained in said container portion in a gas flowing direction; and
  - an orifice, which operates when an opening for connecting said container portion and a gas flowing path on the operation mechanism side is closed, being provided in said gas flow amount control member;
  - wherein said gas flow amount control member controls a gas flow amount with the aid of said orifice by that the member is urged against said opening when said operation mechanism is switched to be released, and that the member is separated from said opening when a gas is filled up in said container.

(2) The valve for use in high pressure gas containers further comprises:
  - an energizing member for energizing said gas flow amount control member in a direction that the member is separated from said opening;
  - wherein the energizing force of said energizing member is smaller than a moving pressure against said gas flow amount control member which is generated by an air flow pressure when said operation mechanism is in a released condition.

(3) The valve for use in high pressure gas containers further comprises:
  - an energizing member for energizing said gas flow amount control member in a direction of the opening;
  - wherein the energizing force of said energizing member is smaller than a moving pressure against said gas flow amount control member which is generated by an air flow pressure when an air is filled up in said container.

(4) The operation mechanism comprises:
  - a valve chamber being formed in said gas exiting path;
  - a valve seat being formed on an opening portion of said gas introducing path;
  - a valve being provided in a freely retrieved manner with respect to said valve seal, and being switchable between a condition that the valve is urged against said valve seat to interrupt an air flow and a condition that the valve is separated from said valve seat to flow air; and
  - an operating means for switching said valve between the interrupting condition and the separated condition.

(5) The operating means comprises:
  - a supporting member being fixed to a body;
  - a connecting member being rotatably supported with respect to said supporting member, one end of which is being connected to said valve; and
  - an operating handle, which is manually operated, being connected to the other end of said connecting member;
  - wherein said connecting member and said valve arc engaged with said supporting member, so that said valve is switched between said interrupted condition and said released condition by rotating said operating handle; and
  - wherein a diameter of said operating handle is less than 5 cm.

(6) The high pressure gas container is filled with oxygen.

(7) The high pressure gas container is portable and compact.

(8) The high pressure gas container is for medical use.

DETAILED EXPLANATION OF THE PREFERRED EMBODIMENTS

The on-off valve for use in high pressure oxygen vessels according to the preferred embodiments of the present invention will be explained, referring to the attached drawings.

Figure 1:
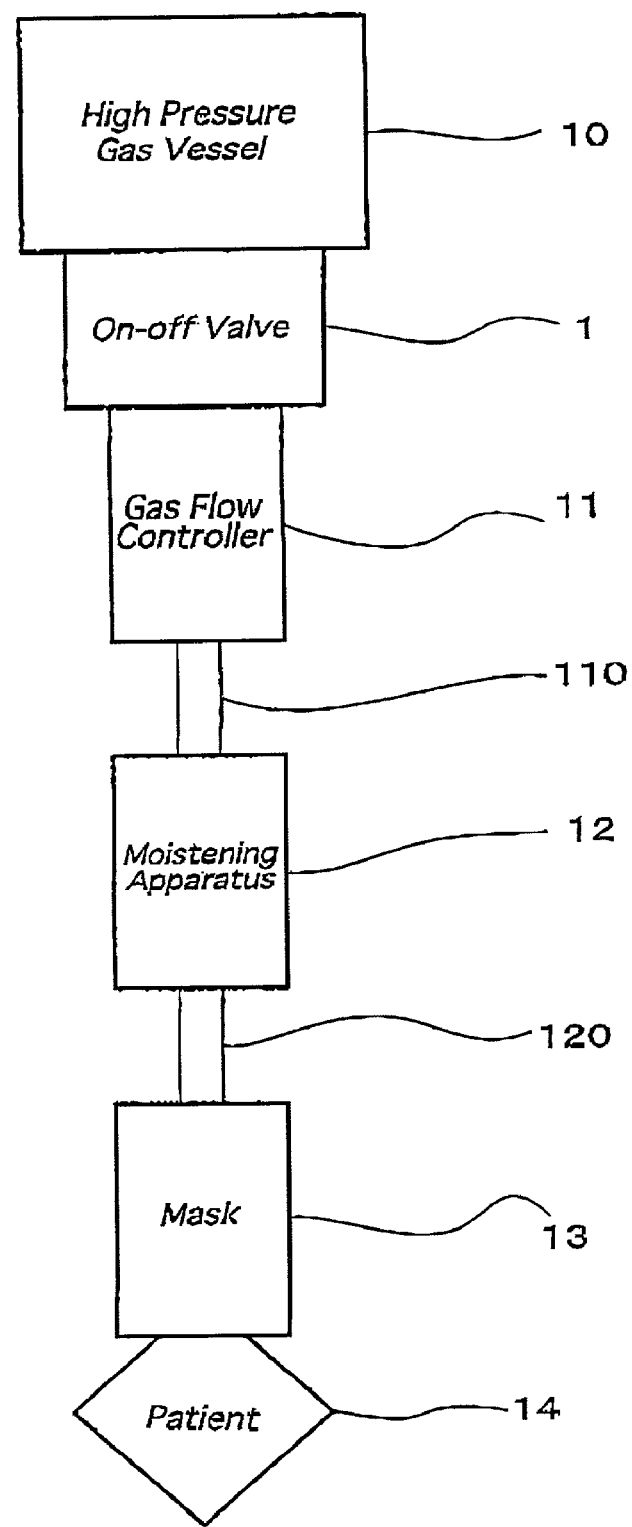
FIG. 1 is a block diagram showing an oxygen inhalation system for medial use where the on-off valve for use in high pressure gas vessels according to the invention is used.

FIG. 1 is a block diagram showing an oxygen inhalation system for medical use where an on-off valve 1 for use in high pressure oxygen vessels according to the invention is used.

A gas high pressure container 10 is constituted of a compact type bomb in order make it portable. For instance the bomb has a capacity of 1~10 liter and an outer diameter of 100–150 mm. The vessel 10 has a connecting member, which is connected to the inside of the vessel 10, to which an on-off valve 1 for use in high pressure oxygen gas vessel is connected, so as to interrupt or open the exhaust of the oxygen gas from the vessel 10. The gas inlet of a gas flow controller 11 is connected to the oxygen gas outlet of the valve 1. To the outlet of the gas flow controller 11, a connecting hole at the upper stream side of a moistening apparatus 12 is connected via a connecting tube 110, and to the other connecting hole at the lower stream side of the moistening apparatus 12 a mask 13 is connected via a connecting tube 120. The mask 13 is applied to the mouth of a patient 14 to supply oxygen. The moistening apparatus 12 or the mask 13 are able to be substituted by others, or are able to be omitted, as occasion demands.

The gas flow amount controller 11 makes the pressure of oxygen gas, contained in the high pressure oxygen vessel, go down to a suitable pressure for supplying the gas to a patient, and to control the gas flow amount to be suitable for patients. In order to do these functions, the controller 11 comprises a pressure reducing portion and a gas flow amount controlling portion; The pressure reducing portion and the gas flow amount controlling portions are connected in series; and the pressure reduction portion is located at an upper stream side and the gas flow amount controlling portion is at a downstream side, when the gas is exhausted. Therefore, the oxygen gas flows into the primary pressure side of the pressure reducing portion first. In the present embodiment, for instance, the pressure reducing portion does not work until the pressure at the primary side (high pressure side) becomes a given pressure or more.

Figure 2:
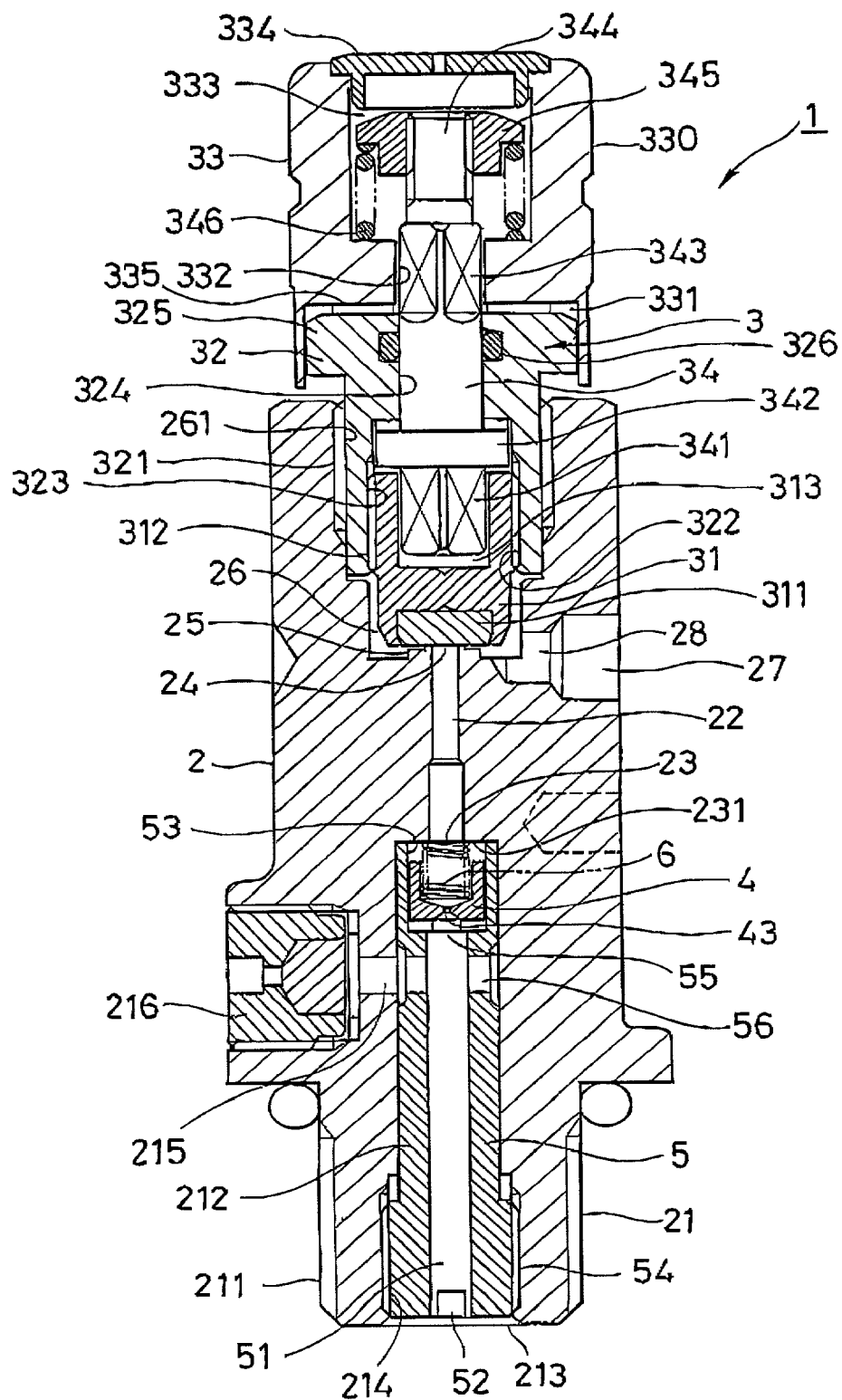
FIG. 2 is a cross sectional view of the on-off valve according to the invention as a whole.

FIG. 2 is a cross sectional view showing the construction of the on-off valve 1 as a whole. The on-off valve 1 comprises a valve body 2, an on-off operating mechanism 3, a flow amount controlling member 4, a holding member 5 for holding the flow amount controlling member 4, and a spring 6 as an energizing means for energizing the flow amount controlling member 4 toward the gas inlet side.

The valve body 2 of the on-off valve 1 comprises a connecting portion 21, which is connected to an opening of said high pressure oxygen gas vessel 10, at the basic end portion thereof. Around the outer surface of the connecting portion 21, is formed a male thread 211, which is engaged with a female thread formed inside of the opening of the high pressure gas vessel 10. Inside of the connecting portion 21, is provided an inserting portion 212 into which the holding member 5 is inserted; and on the basic end of the connecting portion 21, an insertion opening 213 is provided for the holding member 5.

At the top end of the inserting member 212, is connected a flow path 22. One end of the flow path 22 is connected with the inserting portion 212 through the connecting opening 23. The other end of the flow path 22 is connected to a valve chamber 26 via an opening 24.

The holding member 5 is inserted into the inserting portion 212. In the center of the holding member 5, a flow path 51 is formed in a vertical axis direction. The basic end of the flow path 51 constitutes an inlet 52, which opens to the vessel 10; and the top end portion of the flow path 51 is connected to the holding portion 53, which is for holding the flow amount controlling member 4 via an opening 55. The holding portion 53 has a larger diameter than that of the flow path 51 and is formed in the holding member 5 by hollowing the top end of the member 5.

Between the holding portion 53 and the inlet 52, a hole 56 is formed, so that the flow path 51 is connected to the safety valve 216 via a path 215 formed in the valve body 2. Around the basic end of the holding member 5, is formed a male thread 54 which is engaged with a female thread 214 formed inside of the inserting portion 212 of the valve body 2.

In the flow amount control member 4, which is held in the holding portion 53, a spring 6 is contained as an energizing member. The spring 6 is provided between a surface 231, which is formed around the connecting opening 23, and the flow amount control member 4 to energize the flow amount control member 4 in a direction for separating it from the opening 23.

In this manner, along the inlet path of oxygen gas provided from the container 10 to the valve chamber 26, the flow path 51, the holding portion 53 and the flow path 22 are formed.

Within the side surface of the valve body 2, an outlet 27 is formed, which is connected to the valve chamber 26 via an outlet path 28. To the outlet 27, the flow amount controller 11 is connected.

The valve chamber 26 has an opening at the top end side of the valve body 2; in the opening portion the on-off operating mechanism 3 is mounted. The mechanism 3 comprises said valve chamber 26, said valve seat 25, a valve 31, a supporting member 32, a handle 33 for moving the valve 31 advance or retreat in a retreat, and a connecting member 34 which connects the operating handle 33 and the valve 31 so that they are able to be rotated as a united body.

On the inner surface of the opening portion of the valve chamber 26, a female thread 261 is formed, to which the male thread 321 fanned on the outer surface of the supporting member 32 is engaged. In the bottom end portion of the supporting member 32, a valve holding portion 322 is formed. The valve 31 is held in the valve holding portion 322 by engaging a female thread 323 formed on the inner surface of the valve holding portion 322 and a male thread 312 on the outer surface of the valve 31 together. In the center of the supporting member 32, a supporting hole 324 is formed through which the connecting member 34 is inserted. The valve chamber 26 is kept to be airtightened with the aid of an O-ring 326, which is buried, and a packing 335.

The connecting member 34 is inserted into the supporting hole 32 and therefore supported by the supporting member 32. The member has a valve connecting portion 341, which has a rectangular cross-section, and a flange portion 342 on its basic end; The member further has a handle connecting portion 343, which also has a rectangular cross-section, on its other end. The other end protrudes from the supporting hole 32, and the handle connecting portion 343 has a bolt 344, which is protruded from the top end of the handle connecting portion 343.

In the valve 31, an engage portion 313, which is engaged to the valve connecting portion 341 is formed. The connecting member 34 and the valve 31 are connected together by means of the engaging portion 313 and the valve connecting portion 341, so that the member 34 and the valve 31 are able to be rotated as a united body. This connecting structure has a degree of freedom, so the valve 31 is able to move in an axis direction while rotating. Therefore, the connecting member 34 and the valve 31 are rotated simultaneously and the valve 31 is able to move in the axis direction in accordance with the rotating amount with the aid of the engagement of the male thread 312 and the female thread 323. It should be noted that at the top end surface of the valve 31, i.e. the surface where the valve 31 is urged to the valve seat 25, a sealing member (seat disk) 311 is provided in a buried manner.

The operating handle 33 comprises an concave portion 331 for holding a head portion 325 of the supporting member 32, a connecting hole 332 formed in the center portion, a grasp 330, and a spring holder portion 333 formed in the grasp 330. Between the operating handle and the supporting member 32, a packing 335 is inserted.

The connecting bole 332 has a rectangular cross-section and is constituted such that the hole is engaged with the handle connecting portion 343 of the connecting member 34 so that the handle and the connecting member are able to rotated in a united body. That is to say, when an operator rotates the operating handle 33 with the grasp 330, the connecting member 34 is rotated with the handle 33.

To the bolt portion 344 of the connecting portion 34, which is protruded into the spring holder 333 of the operating handle 337 a nut 345 for the spring is engaged. Between the nut 345 and the handle 33, a spring 346 is mounted in a compressed manner. With the aid of the spring 346, the operating handle 33 is urged against the supporting member 34 to enhances the sealing effect of the packing 335. A cap 334 is provided on the spring holder 333.

The on-off operating mechanism 3 is arranged such that the valve 31 is rotated via the connecting member 34 and moved in an axis direction by rotating the operation handle 33. According to this operation, the valve function can be switched between an interrupted condition (valve-off condition), where the gas does not flow outside because the sealing member 311 provided at the top end surface of the valve 31 is being urged against the valve seal 25, and a released condition (valve-on condition), where the gas can flow out because the sealing member 311 is being separated from the valve seat 25 to open the opening 24.

Figure 3:
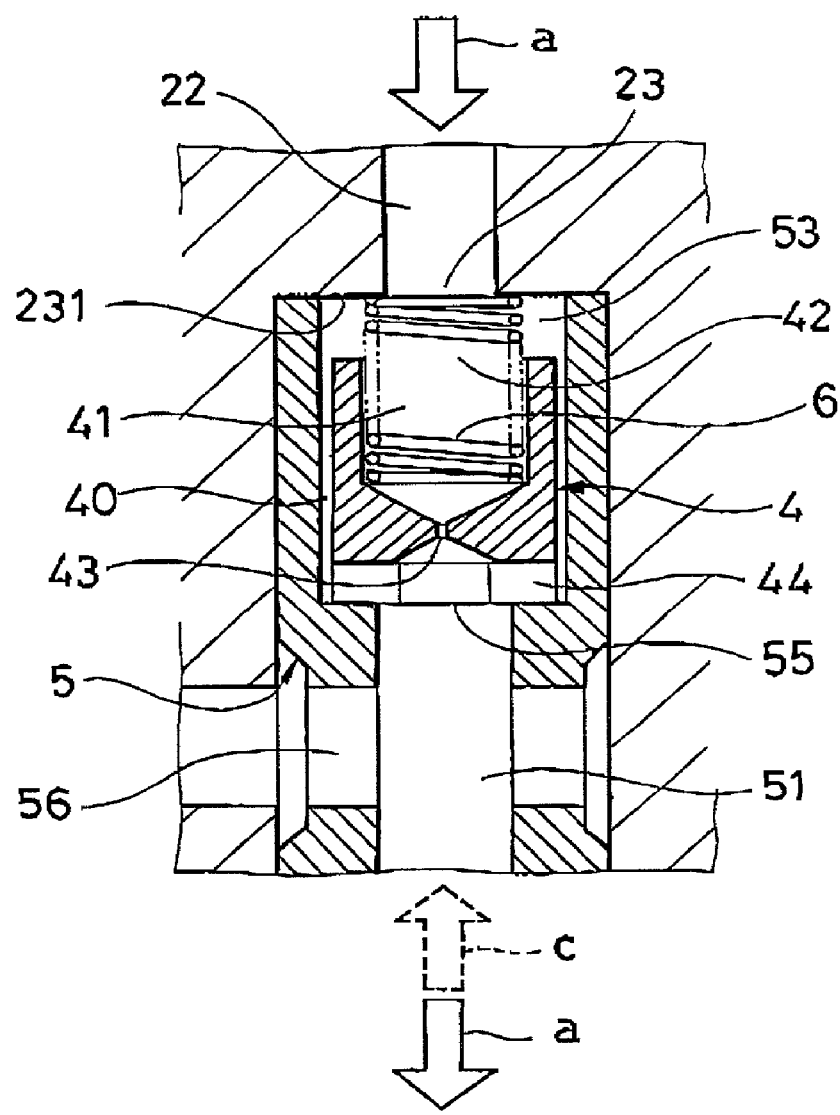
FIG. 3 is a partial cross sectional view depicting a construction of a gas flow amount controlling member and the containing portion therefore in an enlarged scale.
Figure 4:
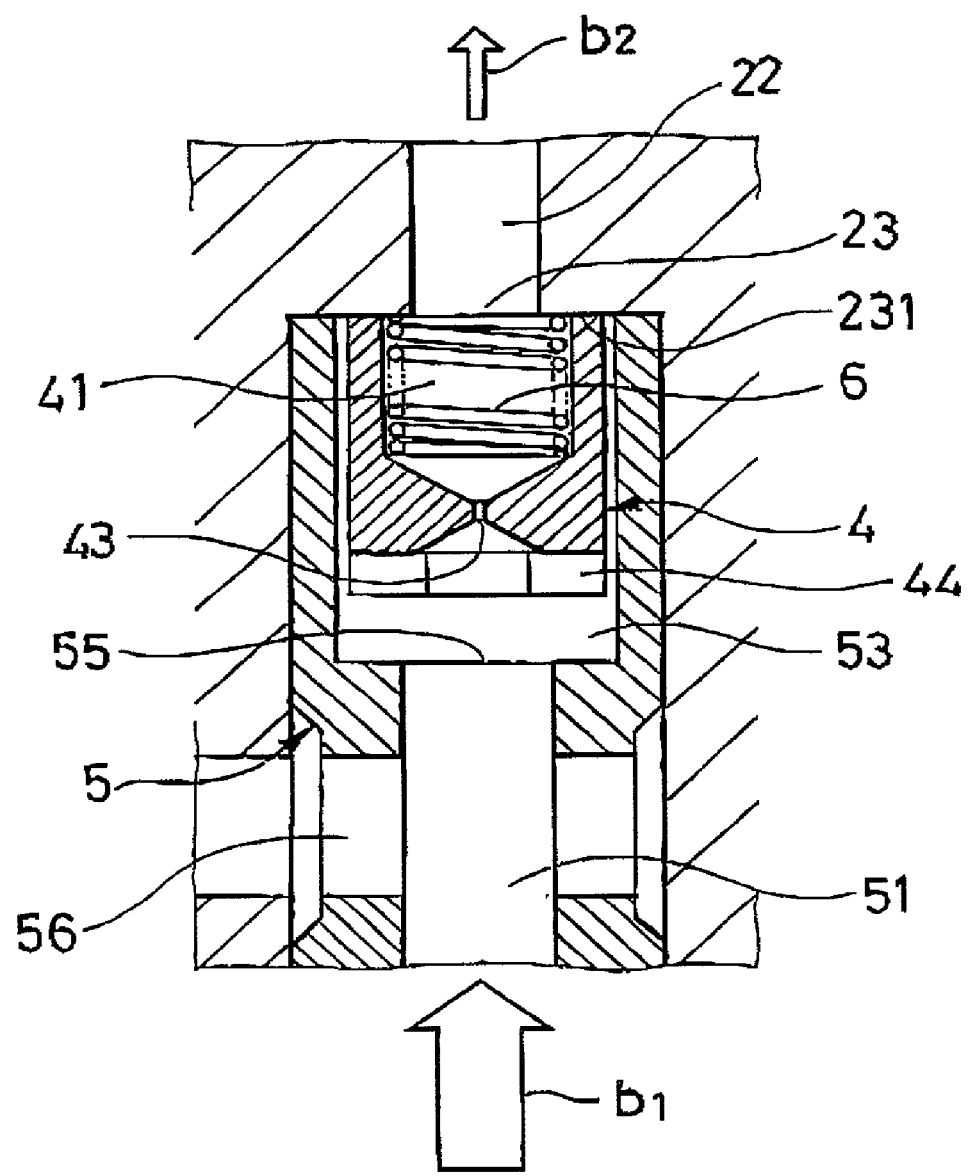
FIG. 4 is also a partial cross sectional view illustrating a construction of a gas flow amount controlling member and the containing portion therefore in an enlarged scale.

The flow amount controlling member 4 held in the holding member 5 will be explained below. FIGS. 3 and 4 are partial cross-sectional views showing the flow amount controlling member 4 and the holding portion 53 in an enlarged manner. FIG. 3 shows the condition of the flow amount controlling member 4 when the on-off valve is interrupted (close); and FIG. 4 illustrates the condition of the flow amount controlling member 4 when the on-off valve is open (particularly, just after the valve is opened).

The flow amount controlling member 4 has a cylindrical hollowed shape whose outer surface follows the inner shape of the holding portion 53; the inner hollowed portion 41 constitutes an opening end 42 which opens toward the connecting hole 23; and at an opposite end, an orifice 43 is provided. In this embodiment, the opening end 42 is located at the connecting hole 23 side, and the orifice 43 is located at the high pressure oxygen gas container 10 side.

In the hollowed portion 41, a spring 6 is contained in a compressed manner as an energizing member. One end of the spring 6 is urged against the receiving surface 231, which is formed around the connecting hole 23; while the other end is urged against a bottom surface of the hollowed portion 41. Thus, the spring energizes the flow amount controlling member 4 so as to separate it from the connecting hole 23. The outer diameter of the flow amount controlling member 4 is sufficiently smaller than the inner diameter of the holder 53, so that a sufficient space is provided between the inner wall of the holder 53 and the outer surface of the flow amount controlling member 4, through which a gas can flow smoothly. The flow amount controlling member 4 has a groove 44 at the gas container side so as to keep a flow path when a gas is being filled in the container.

The flow amount controlling member 4 moves between the position that the opening end 42 is urged against the receiving surface 231 opposite to the energizing power of the spring 6 and the position that the opening end 42 is separated from the surface 231 with the aid of the power of the spring 6. When the opening end 42 of the flow amount controlling member 4 is made to contact to the receiving surface 231, the orifice 43 functions to restrict the upper limit of the flow amount of the oxygen gas. It is necessary that the flow amount controlling member 4 moves in such a member that the opening end 42 is made contact to the connecting hole 23 so as to surround it, in other words, in such a manner that the connecting hole 23 is completely closed by the flow amount controlling member 4. The hollowed outer surface functions as a guide surface so that the orifice 43 can move in the holder 53 while keeping its posture properly.

The hollow portion 41 functions as a flow path for the oxygen gas which has passed through the orifice 43 when the flow amount controlling member 4 closes the connecting hole 23.

Therefore, only the gas, which has passed through the orifice 43, flows into the downstream side of the orifice 43.

On the other hand, when the gas container 10 becomes empty, oxygen gas is supplied from the outside through the open-close valve 1. (The gas flow is shown by an arrow a in the figures). In this case, the flow amount controlling member 4 is being separated from the connecting hole 23 by the spring 6, as shown in FIG. 3. In addition, the flow paths other than the orifice 43, i.e. the space 40 between the outer surface of the member 4 and the holding portion 53, and the grove 44, are kept so that a gas flow can be for obtaining a sufficient flow amount of gas in order to fill the container. That is to say, the container can be filled smoothly without separately providing any bypath.

The function of the flow amount controlling member 4 will be explained more concretely. For instance, assuming the case that no flow amount control member 4 is provided, when the valve 31 moves to the open position by the on-off operating mechanism 3, oxygen gas comes up to the primary side space of the flow amount controller 11 instantly by the gas pressure in the high pressure oxygen gas container 10. Since a high pressurized gas goes through the path from the on-off valve to the flow amount controller 11, it is necessary to keep a path having a sufficient strength.

However, such a path is mostly designed to be short in order to save the cost for manufacturing and to make the container compact taking transporting convenience into consideration.

Therefore the on-off valve and the flow amount controller 11 are provided to be close to each other, and thus a total capacity from the on-off valve 1 to the primary side space of the flow amount controller 11 becomes small. Further, the flow amount controller 11 does not work until the pressure in the primary side reaches a predetermined pressure. In other words, a closed space having a small capacity is formed at the downstream side of the on-off valve 1 until the pressure in the primary side becomes the predetermined pressure. While, a flow amount controller where the pressure reduced portion is released or in a flow amount controller which does not have a pressure reduced portion, such a closed space is formed even if the flow amount controller is set at flow amount zero. (in other words, even when the valve in closed)

If a high pressurized gas is instantaneously filled into such a space having a small capacity, the gas in the closed space becomes in a condition of adiabatic compression and thus a heat is generated. At the same time, a friction heat is also generated by the fact that the gas passes through a narrow space between the opening 24 of the valve seat and the sealing member 311 with a high speed. In addition, oxygen gas per se has a nature as an essential for ignition. When these conditions come at once, there is a fear that in an instant that the on-off valve 1 is open the sealing member 311, oil used when members are processed, the other oils, like rubrication, or dusts are ignitioned.

While, according to the on-off valve 1 for use in a high pressurized oxygen gas container according to the present invention, in an instant when the valve 31 is moved to the on position (when the valve is opened), oxygen gas flows from the high pressurized gas container 10 into the valve chamber 26. At this time, at almost the same time that the oxygen gas starts to flow, the flow amount controlling member 4 is urged against the connecting hole 23 side by the gas pressure so as to close the hole 23.

As shown in FIG. 4 by the arrows b1 and b2, which represent the gas flow, since the flow amount of the gas going into the closed space at the downstream side becomes small by the function of the orifice 43, the pressurizing speed in the closed space becomes so slow that the heat generation due to the adiabatic compression is reduced.

The reduced amount of gas is sufficient for being supplied to the flow amount controller 11 and is so small to a degree that the heat generation due to the adiabatic compression can be prevented. The orifice is just required to work to prevent adiabatic compression when the valve is opened; thus after the gas flow amount is stabilized, the controller is separated from the connecting hole 23 by the spring 6, even if the gas is still being supplied into the container. This is caused by the fact that the energizing force of the spring 6 is set much stronger than the moving pressure, which is applied at the flow amount controlling member 4, generated when gas flows under the normal gas flowing condition (oxygen being supplied to a patient).

In this manner, by arranging that the orifice 43 only works just after the valve is opened, an advantage can be obtained that when the gas supply amount is increased after the valve is opened, the orifice 43 does not disturb the gas supply. Particularly, in case that the amount of the gas flow restricted by the orifice 43 is smaller than the maximum flow amount of the flow amount controller 11, which is located at a down stream side, the flow amount when the gas is normally supplied can be obtained sufficiently.

Furthermore, in such a case that the gas supply amount becomes suddenly high during when oxygen is supplied to a patient, the flow amount controlling member 4 moves instantaneously and the orifice 43 works to reduce the sudden increase of the gas supply to the patient; therefore, troubles for patients can be prevented before they happen.

The diameter of the grasp 330 of the operating handle 33 is about 20~40 mm, which is suitable to the diameter of the body 2. Since the high pressurized oxygen gas container 10 is designed to be compact taking the portability into consideration, the on-off valve 1 for use in high pressure oxygen gas container is also designed to be compact, and the operating handle 33 does not protrude from the body 2. Such a construction has an advantage when the container is mounted in ambulance cars, because the container does not need so much space. However, since the diameter of the grip 330 is small, a greater grasping power is required to operate the grip, therefore it becomes difficult to open the on-off operating mechanism 3 slowly. Thus, the operation is apt to move the valve 31 to the opening position at once. However, according to the invention, since the gas flow amount is reduced by the flow amount adjusting member 4, it is not necessary for an operator to pay attention for the operation of the handle 33.

Figure 5:
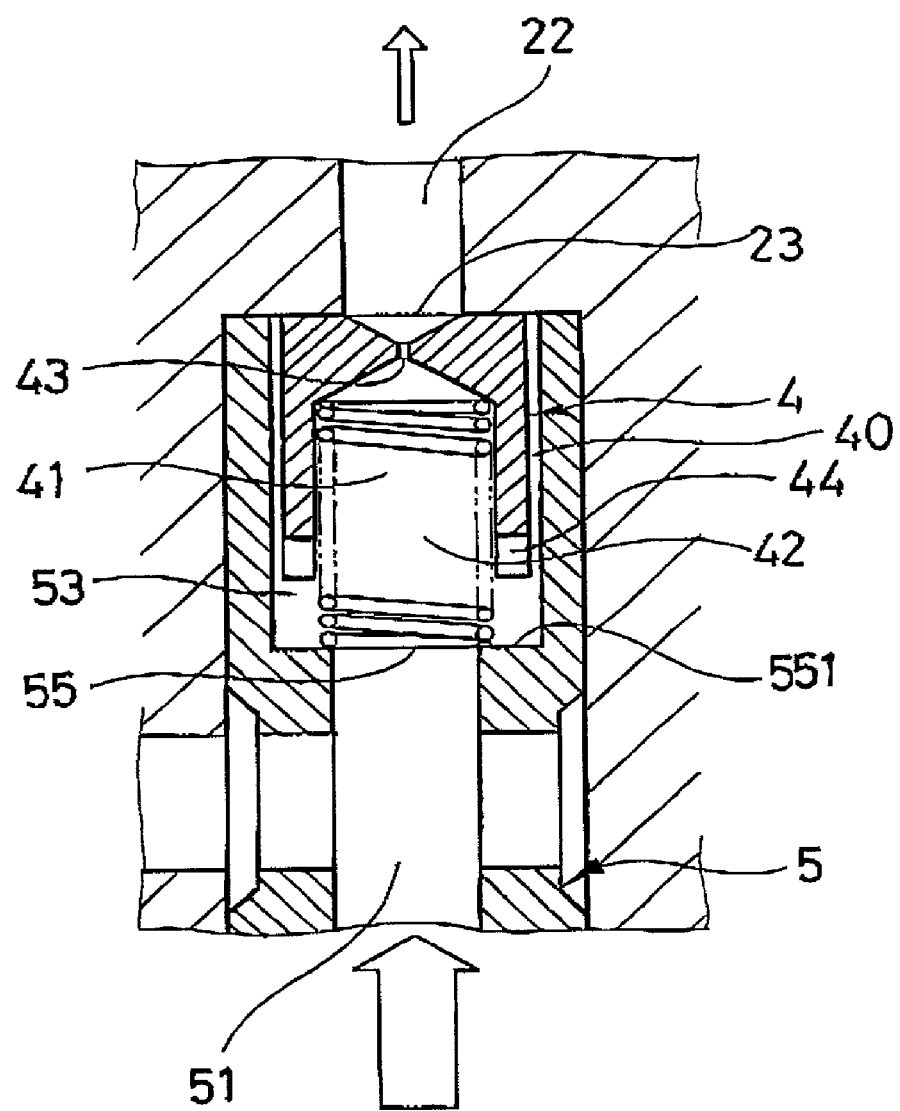
FIG. 5 is a partial cross sectional view representing a construction of a gas flow amount controlling member and the containing portion therefore according to another embodiment in an enlarged scale.
Figure 6:
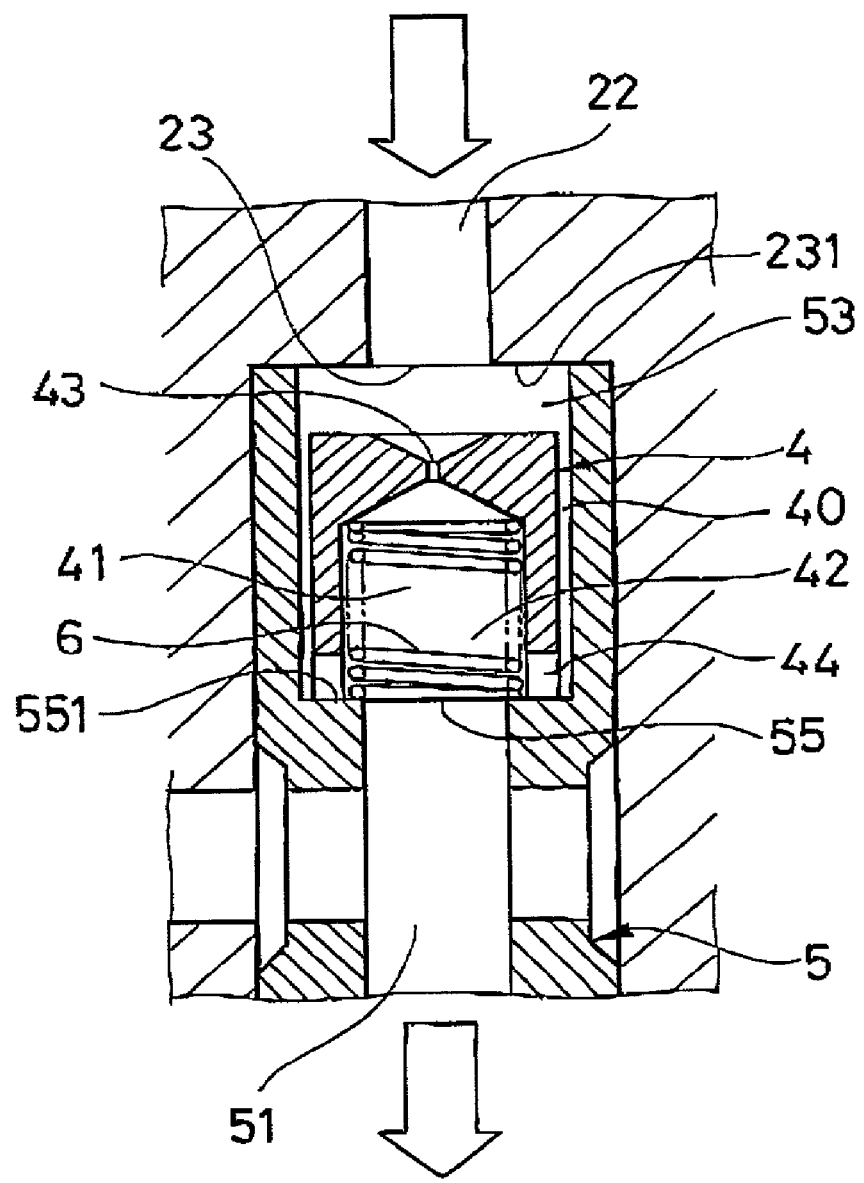
FIG. 6 is a partial cross sectional view showing a construction of a gas flow amount controlling member and the containing portion therefore according to another embodiment in an enlarged scale.

FIGS. 5 and 6 are partial cross-sectional views showing a construction the flow amount controlling member 4 and the holding portion 53 shows other embodiments according to the invention in an enlarged scale.

FIG. 5 shows a condition that the on-off valve 1 for use in high pressurized oxygen gas containers is closed and also a condition that the valve 1 is opened; and FIG. 6 illustrates a condition that oxygen gas is being filled in the high pressurized oxygen gas container 10.

In this construction, the flow amount controlling member 4 is attached in an opposite direction, the orifice 43 is located at the connecting hole 23 side and the spring 6 is inserted between the surface 551 at the opening 55 side and the flow amount controlling member 4. In order to keep the path for the gas flow when oxygen gas is being filled, a grove 44 is formed at the opening end 42 side. According to this construction, the connecting hole 23 is always closed with the flow amount controlling member 4 except for the case that oxygen gas is being filled in the high pressurized oxygen gas container 10, so that the flow amount of the high pressurized oxygen gas is always limited by the orifice 43. The spring 6 has a function to urge the flow amount controlling member 4 against the connecting hole 23 while keeping the member 4 with a proper posture. When oxygen gas is being filled, the flow amount controlling member 4 is being separated from the connecting hole 23 with the aid of gas pressure from the outside, as shown in FIG. 6. A gas flow path, which is sufficient for flowing oxygen gas being filled into the container, is provided by the space 40 and the groove 44.

It should be noted that the spring 6 may not be inserted into the flow amount controlling member 4. In this case, when the valve is opened, the flow amount controlling member 4 is urged against the connecting hole 23 with the aid of a flow-out pressure of the gas contained in the high pressurized oxygen gas container 10 to close the hole 23, so that the instant increase of gas pressure caused by the flow-out gas in the closed space is also limited.

As a result, the heat generation according to the adiabatic compression is also reduced.

Further, when a gas is supplied into the high pressurized gas container 10, the flow amount controlling member 4 is separated from the connecting hole 23 with the aid of the gas flow in pressure when the gas is supplied so as to keep the gas flow path, because the energizing force of the spring 6 is set to be smaller than the moving pressure applied to the gas flow amount controlling member 4 when the gas is supplied. Therefore, there is no need to additionally provide a bypass for supplying gas.

According to the above mentioned construction, the flow amount controlling member 4 can face either the directions shown in FIG. 3 or FIG. 5. Further, the orifice may be provided in the center portion of the cylindrical body of the flow amount controlling member 4.

The above-mentioned embodiments refer a manual type on-off valve, however, it may be possible to provide an on-off valve which is operated with the aid of an actuator. In such valves, it is sometimes difficult to slowly move the, valve to the opened position, so the present invention is particularly useful.

As stated above, the on-off valve for use in a highly pressurized gas container according to the present invention is designed to reduce the pressurizing speed in a closed space formed between the valve and the apparatus connected to the downstream side; as a result the heat generation due to the adiabatic compression is reduced. Therefore, if there is a space where the pressurizing speed is suddenly increased, the space can be substantially considered as the closed space in the present invention, For instance, a space where a flow path having a fine aperture is provided is assumed; if the gas flow amount coming into the space with a high pressure is sufficiently large in comparison to the flow amount going out through the aperture, the speed pressurizing speed is suddenly increased and then a heat generation due to adiabatic compression could be caused. Such a space where the gas amount going out is very small with respect to the flow amount of gas coming in can be substantially said as a close space.

According to the present invention, a sudden increase of gas pressure in the closed space when the valve is open is reduced by the flow amount controlling member, so that heat generation due to adiabatic compression can be reduced. Further, when filling the container with gas, the gas flow for filling is not disturbed. Therefore, gas can be filled in the container smoothly without providing a bypath.

Further, according to the present invention, the flow amount controlling member is energized in a direction that the member is being separated from the connecting hole with the aid of energizing member. Therefore, the connecting hole can be surely closed, so that the sudden increase of gas pressure in the closed space due to the flow in gas can be surely restricted. Furthermore, since the energizing member has a force smaller than the pressure of gas flow-in the energizing member does not disturb the gas filling and there is no necessity to provide a particular path for filling the gas.

Furthermore, according to the present invention, in a case that the gas flow is interrupted by urging the valve against the valve seat, it is also restricted that a heat is generated due to the friction between the gas and the valve or the valve seat when the gas goes through the space between the valve seat and the valve.

Furthermore, according to the present invention, in the case that the handle is arranged to be manually rotated to make the valve on or off, even if the diameter of the handle is so small that it is hard for the operator to grasp it and then hard to release the valve slowly, the sudden increase of the gas pressure can be restricted in the closed space.

In a case that the gas is oxygen, the gas per se works as an essential for ignition. However, according to the present invention, since the pressurizing space is restricted, the heat generation due to the adiabatic compression or friction can be reduced. As a result, the trouble such as ignition can be prevented.

Moreover, in compact and portable type gas containers, the operator for using the on-off valve is not specified and therefore the operators sometimes are not skilled to use the high pressurized gas containers. However, according to the present invention, in the case that such a non-skilled operator operates the container, the heat generation due to the adiabatic compression or friction can be restricted. Further, the invention is particularly useful for compact type containers, because in such a compact type containers the closed space formed between the container and the apparatus to be connected to the outlet side of the on-off valve is small and heat generation due to the adiabatic compression of gas is apt to be produced.

Furthermore, when the container is used for a medical purpose, it is sometimes necessary to urgently open the valve depending on the condition of the patient. In such a case, however, it is sometimes difficult to observe the cautions such as that "Operate the handle slowly and open the valve gradually". However, according to the invention, the trouble due to the heat generation or ignition can be reduced because the gas flow amount is adjusted with the aid of flow amount controlling member.

What is claimed is:

1. An open-close valve for use in high pressurized gas containers comprises:

an inlet being connected to a high pressurized gas container;

an outlet being connected to a close space;

an on-off operation mechanism for controlling a gas flow between said inlet and said outlet between an interrupted condition and an opening condition, being provided between said inlet and said outlet;

a gas flow-in pat for connecting said on-off operation mechanism and said inlet;

a gas flow-out path for connecting said on-off operation mechanism and said outlet;

a flow amount controlling member comprising a containing portion being provided in said inlet;

said flow amount controlling member for restricting an upper limit of gas flow amount through said inlet when said valve is open, being contained in said containing portion in a freely movable condition;

an orifice, which functions when a connecting hole between said containing portion and said gas flow-out path of said on-off operation mechanism side is closed, being provided in said flow amount controlling member; and bias member for biasing said flow amount controlling member against said connecting hole;

wherein said flow amount controlling member acts to restricts a flow amount by being urged against said connecting hole, when said on-off operation mechanism is switched to open the valve at a first time frame; and when gas is filled into said high pressure gas container at a second time frame, following said first time frame, after gas flow is stabilized, said flow amount controlling member is separated from said connecting hole to open said orifice;

wherein a biasing force of said bias member is smaller than a first moving pressure applied to said flow amount controlling member caused by gas flowing-in pressure when said on-off operation mechanism is released during said first time frame, and wherein the biasing force of said bias member is greater than a second moving pressure applied to said flow amount controlling member caused by gas flowing during said second time frame, such that the gas flow amount controlling member is separated from the connecting hole.

2. An open-close valve for use in high pressurized gas containers according to claim 1 further comprises:

an energizing member for energizing said flow amount controlling member in a direction that the member is separated from said connecting hole;

wherein, an energizing force of said energizing member is smaller than a moving pressure applied to said flow amount controlling member which is caused by gas flowing-in pressure when said on-off operation mechanism is released.

3. An open-close valve for use in high pressurized gas containers according to claim 1, wherein said on-off operation mechanism comprises:

a valve chamber being formed in said gas flowing-out path;

a valve scat being formed in said gas flowing-in path;

a valve body moving freely with respect to said valve seat and being switchable between an interrupted condition where said valve is urged against said valve seat to interrupt a gas flow and an open condition where said valve is separated from said valve scat to make the gas flow possible; and a switching means for switching the valve between said interrupted condition and the open condition.

4. An open-close valve for use in high pressurized gas containers according to claim 3, further comprising an operating means for operating said on-off valve;

wherein said valve comprises:

a supporting member being fixed to said valve body;

a connecting member being supported by said supporting member in a rotatable manner, one end of which is connected to said valve;

an operating handle, which is operated in a manual manner, being connected to the other end of said connecting member;

wherein said connecting member or said valve is engaged to said supporting member, and wherein said valve is switched between said interrupted condition and said open condition by rotating said handle; and wherein the diameter of said handle is 5 cm or less.

5. An open-close valve for use in high pressurized gas containers according to claim 1, wherein said container is filled with oxygen.

6. An open-close valve for use in high pressurized gas containers according to claim 1, wherein said container is portable and compact.

7. An open-close valve for use in high pressurized gas containers according to claim 1, wherein said container is used for a medical purpose.

* * * * *